US00PP34912P2

(12) United States Plant Patent
NeSmith

(10) Patent No.: US PP34,912 P2
(45) Date of Patent: Jan. 17, 2023

(54) SOUTHERN HIGHBUSH BLUEBERRY PLANT NAMED 'TH-1093'

(50) Latin Name: *Vaccinium corymbosum*
Varietal Denomination: 'TH-1093'

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/862,784

(22) Filed: Jul. 12, 2022

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Thomas Horstemeyer, LLP

(57) ABSTRACT

A new and distinct cultivar of *Vaccinium* plant named 'TH-1093', characterized by a combination of early to mid-season ripening and flowering; large berries with good flavor, firmness, and scar; and a medium chilling requirement of about 350 to 450 hours, or more, below about 45° F.

6 Drawing Sheets

Botanical designation: *Vaccinium corymbosum.*
Cultivar denomination: 'TH-1093'.

BACKGROUND OF THE INVENTION

The present invention relates to a new and distinct cultivar of southern highbush blueberry plant, botanically known as *Vaccinium corymbosum*, and hereinafter referred to by the cultivar name 'TH-1093'.

The new *Vaccinium corymbosum* 'TH-1093' was first identified by the inventor in 2007 in Griffin, Ga. The new variety 'TH-1093' is early to mid-season for flowering time and ripening. 'TH-1093' has medium to large berries with good scar, color, firmness and flavor as compared to other representative cultivars. It is estimated to have a chilling requirement of about 350-450 hours, or more, below 45° F. when produced under typical low to mid chill production areas in temperate regions. 'TH-1093' is able to produce high-quality fruit when grown in conventional production areas.

'TH-1093' is a product of an open-pollinated cross of *Vaccinium corymbosum* 'MS-840' (Female parent, non-patented breeding selection) X unknown male parent. Seed from this cross was collected in 2004 by D. Scott NeSmith, planted in following years, and the new 'TH-1093' was selected in 2007. The new blueberry plant variety 'TH-1093' has been tested in asexually propagated (by softwood vegetative cuttings) plantings in Alapaha, Ga. since 2013 where it was established for testing and comparing to industry standards. Observations of the resulting 'TH-1093' progeny have shown that the unique features of this new *Vaccinium corymbosum* 'TH-1093' are stable and reproduced true to type in successive generations.

SUMMARY OF THE INVENTION

The new *Vaccinium cultivar* 'TH-1093' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-1093'. In combination, these traits set 'TH-1093' apart from all other existing varieties of southern highbush blueberry known to the inventors:

1. Early to mid-season, flowering before 'MS-840' and later than 'Suziblue' (U.S. Plant Pat. No. 21,167), and 'Rebel' (U.S. Plant Pat. No. 18,138);
2. ripening before 'MS-840' and later than the early variety 'Suziblue' (U.S. Plant Pat. No. 21,167) and 'Rebel' (U.S. Plant Pat. No. 18,138);
3. produces berries that have aromatic, sweet, mildly acid flavor, smaller scar, and are firmer than berries of 'Suziblue' and 'Rebel'; and
4. medium chilling requirement of about 350-450 hours, or more, below about 45° F. (based on comparison of flowering dates with those of known standard cultivars) when produced under typical low to mid chill production areas in temperate regions.

As compared to the female parent 'MS-840', plants of *Vaccinium* 'TH-1093' have a lower chilling requirement, earlier flowering and ripening times, and similar firmness. Male parent is unknown.

Plants of the new *Vaccinium* can also be compared to the commercial early season southern highbush blueberry cultivars 'Suziblue' and 'Rebel'. The new variety 'TH-1093' is early season and begins flowering and ripening later than 'Suziblue' and 'Rebel'. 'TH-1093' has large berries that are firmer and have smaller scar than berries of 'Rebel'. The berries of 'TH-1093' also have lighter blue color, and aromatic, sweet, mildly acid flavor compared to 'Rebel' at Alapaha (Table 1). When compared to 'Suziblue', fruit of 'TH-1093' are smaller, with similar scar and color, but are firmer and have more balanced sweet/acid flavor (Table 1). No notable diseases or other pest problems have been observed for the new variety that are not also common for other varieties. The new variety is estimated to have a chilling requirement of about 350-450 hours, or more, below about 45° F. (based on comparison of flowering dates with those of known standard cultivars) when produced under typical low to mid chill production regions. Additional comparison data of 'TH-1093' with 'Suziblue' and 'Rebel' are presented in the tables below.

Table 1. Plant and fruit ratings for 'TH-1093' and standards grown in Alapaha, Ga. Data represents a 3 Year average (2015, 2016, and 2021). Rating scales are based on a 1 to 10 score, with 1 being the least desirable and 10 being the most desirable. Plants were established in 2013.

TABLE 1

Plant and fruit ratings for 'TH-1093' and standards grown in Alapaha, GA. Data represents a 3 Year average (2015, 2016. and 2021). Rating scales are based on a 1 to 10 score, with 1 being the least desirable and 10 being the most desirable. Plants were established in 2013.

| | 'Suziblue' | 'Rebel' | 'TH-1093' |
|---|---|---|---|
| Berry size | 8.2 | 7.8 | 7.2 |
| Berry scar | 7.3 | 7.0 | 7.2 |
| Berry color | 7.2 | 7.2 | 7.2 |
| Berry firmness | 7.5 | 7.0 | 8.0 |
| Berry flavor | 7.2 | 6.0 | 8.5 |
| Cropping | 7.0 | 5.0 | 5.5 |
| Plant vigor | 8.5 | 7.5 | 8.1 |
| Date of 50% flowering | March 5 | March 4 | March 9 |
| Date of 50% ripening | May 6 | May 4 | May 11 |
| Fruit development period (days) | 62 | 60 | 62 |

BRIEF DESCRIPTION OF THE DRAWINGS

The accompanying colored photographic illustrations show the overall appearance and distinct characteristics of the new cultivar of *Vaccinium corymbosum* 'TH-1093' showing the colors as true as possible. Colors in the photographs may differ slightly from the color values cited in the detailed botanical description, which accurately describes the colors of the new *Vaccinium corymbosum* 'TH-1093'. Photographs were taken of plants grown outdoors in Alapaha, Ga. during different years.

The photograph labeled

Figure 1:
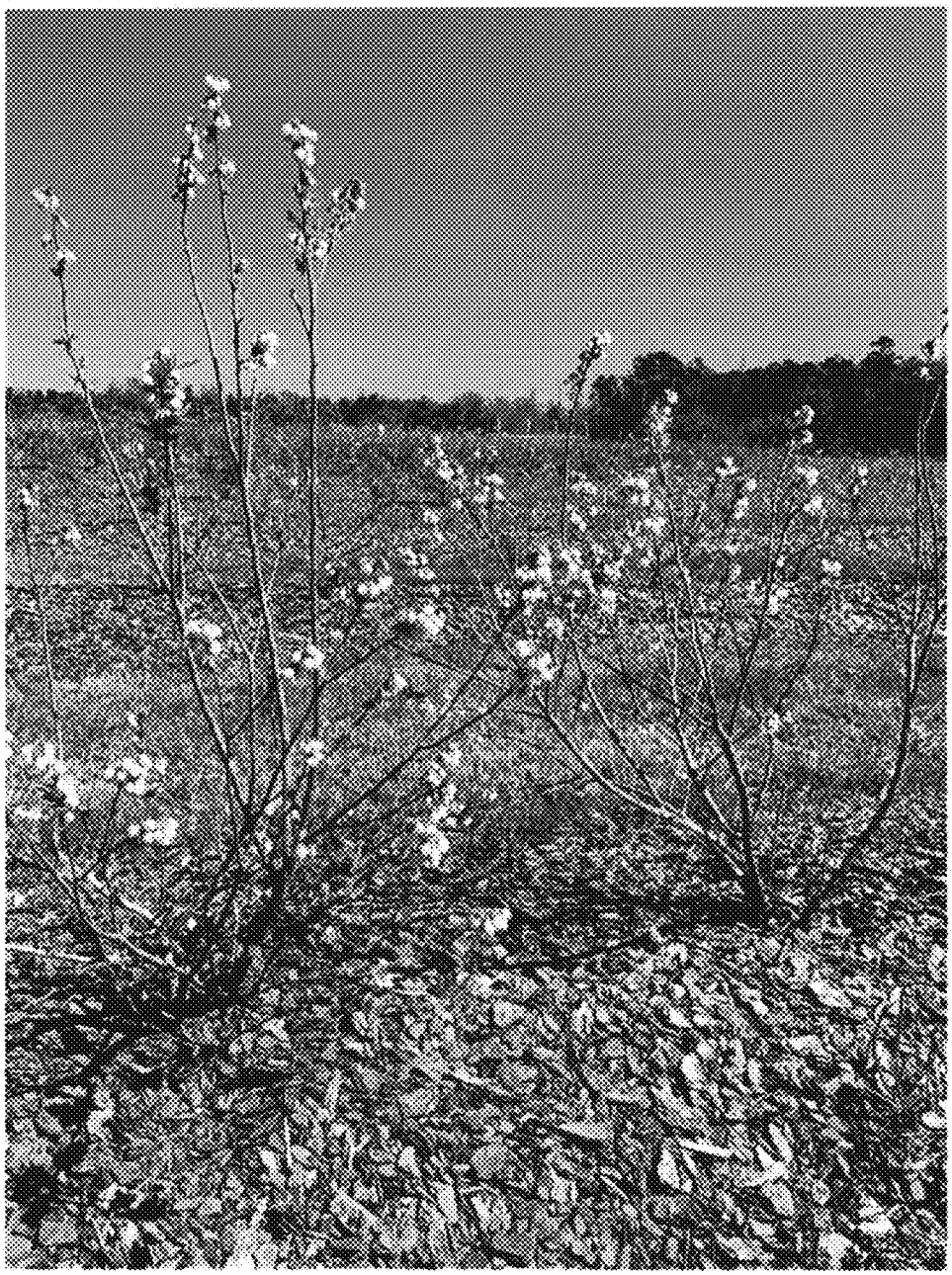
FIG. 1 depicts typical 3-year old plants of 'TH-1093' during flowering. Photographs were taken in March 2019.
Figure 2:
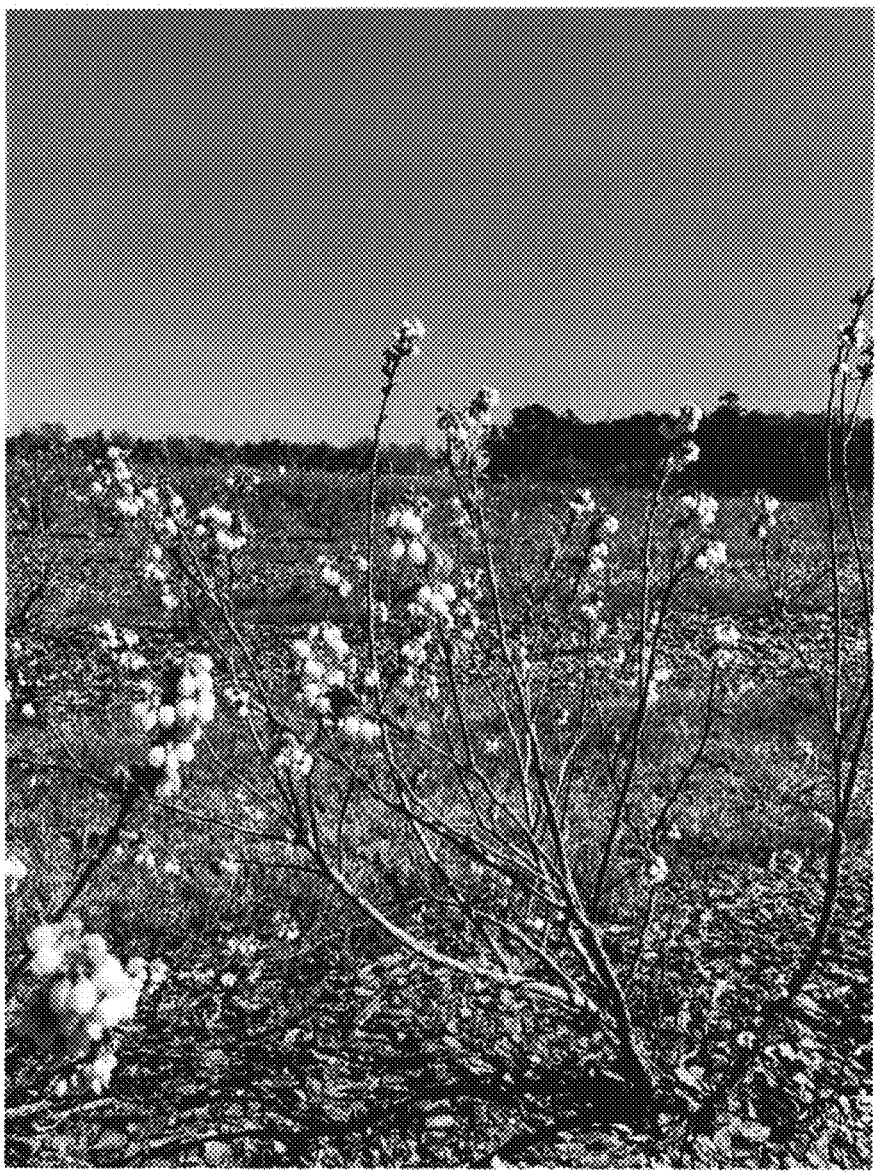

The photograph labeled FIG. 2 was taken in March 2021 and shows a close-up of flowering branches of 'TH-1093'.

Figure 3:
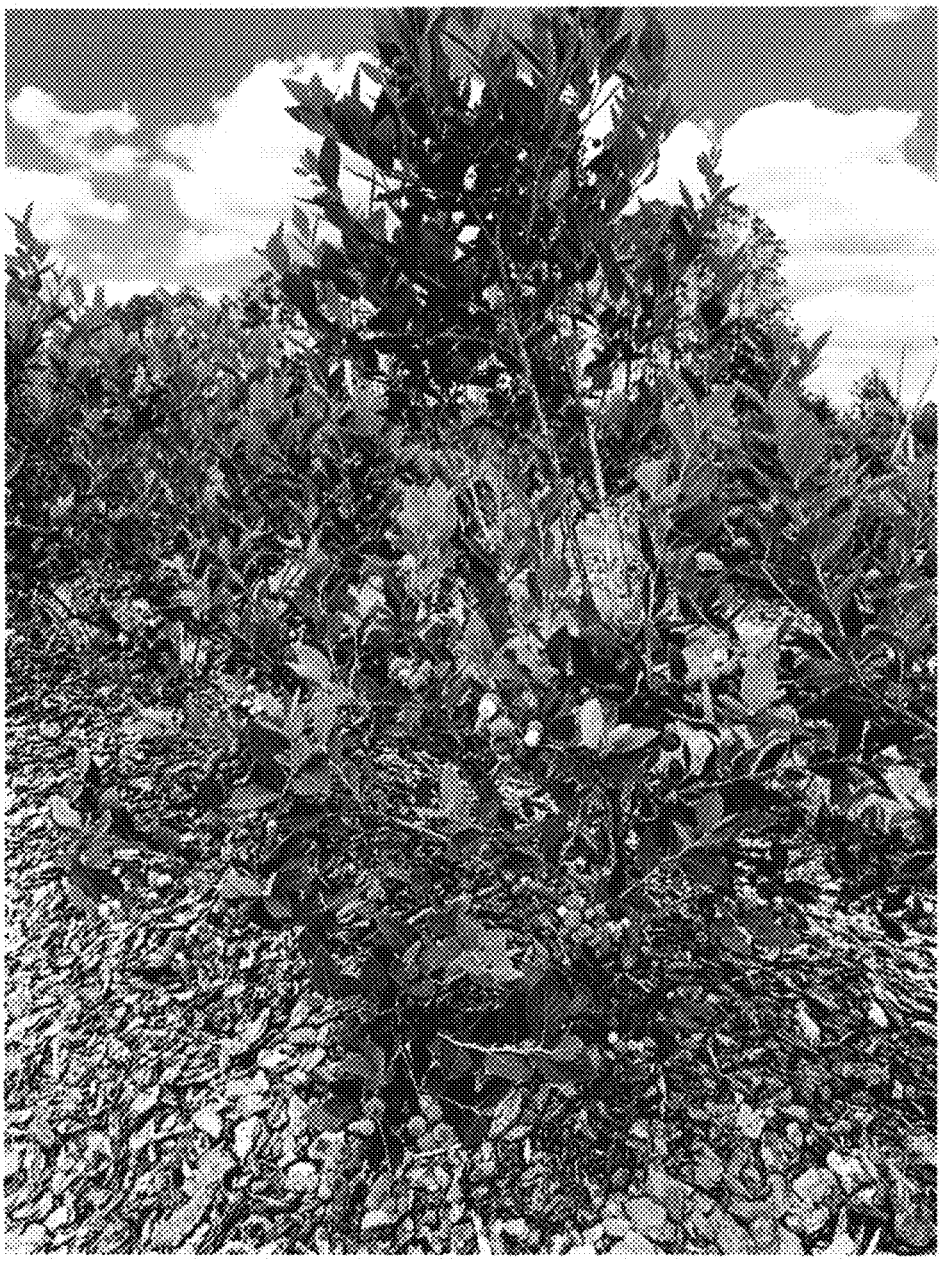

The photograph labeled FIG. 3 depicts 3-year old 'TH-1093' plants during fruit ripening. Photographs were taken in May 2019.

Figure 4:
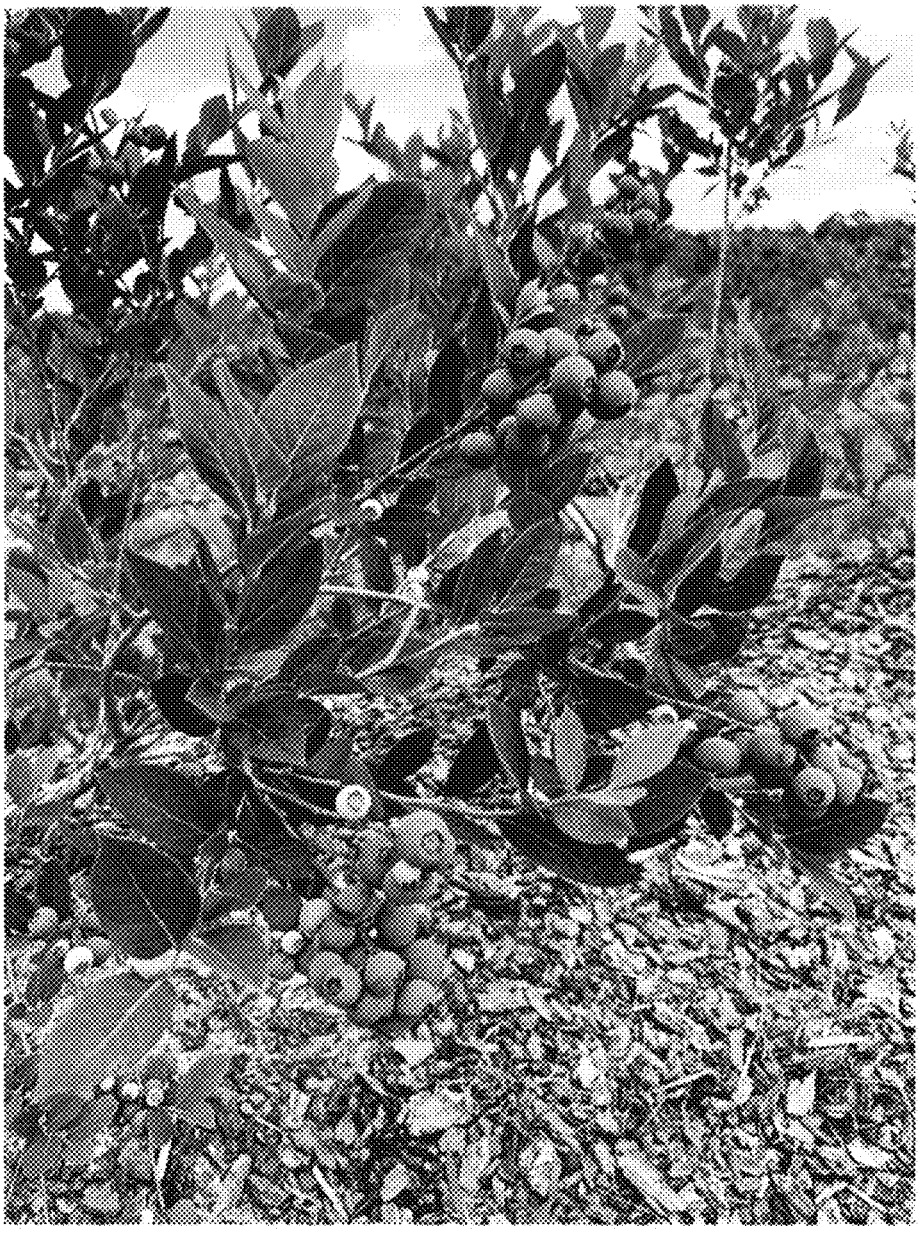

The photograph labeled FIG. 4 depicts a close-up view of 'TH-1093' fruit as it matures showing good scar and color, taken in May 2019.

Figure 5A:
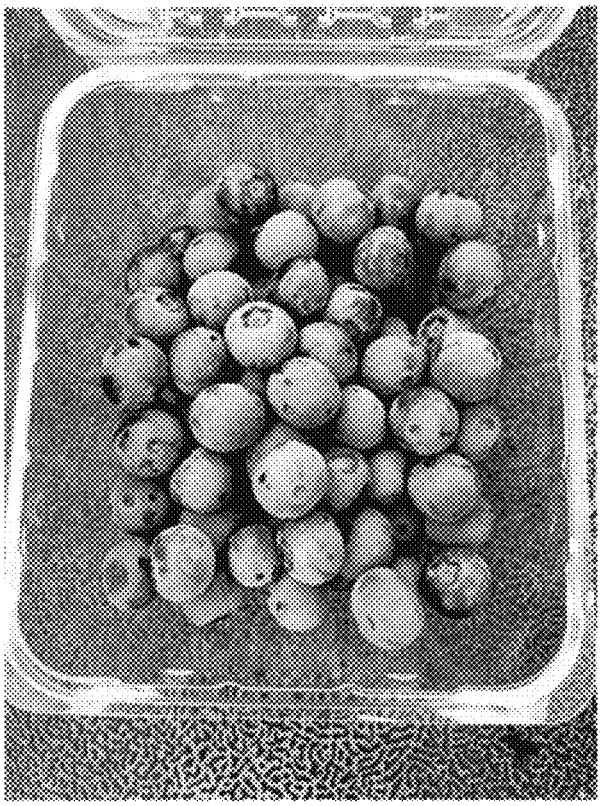
Figure 5B:
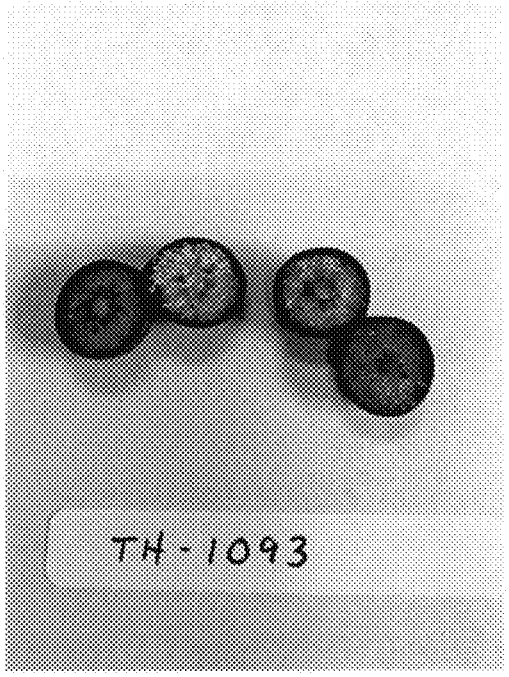

The photographs labeled FIGS. 5A-5B depict close-up views of 'TH-1093' fruit. FIG. 5A is a close-up view of fruit of 'TH-1093' in a container, and FIG. 5B shows a cross sectional view of the interior of the fruit taken in May 2021.

Figure 6:
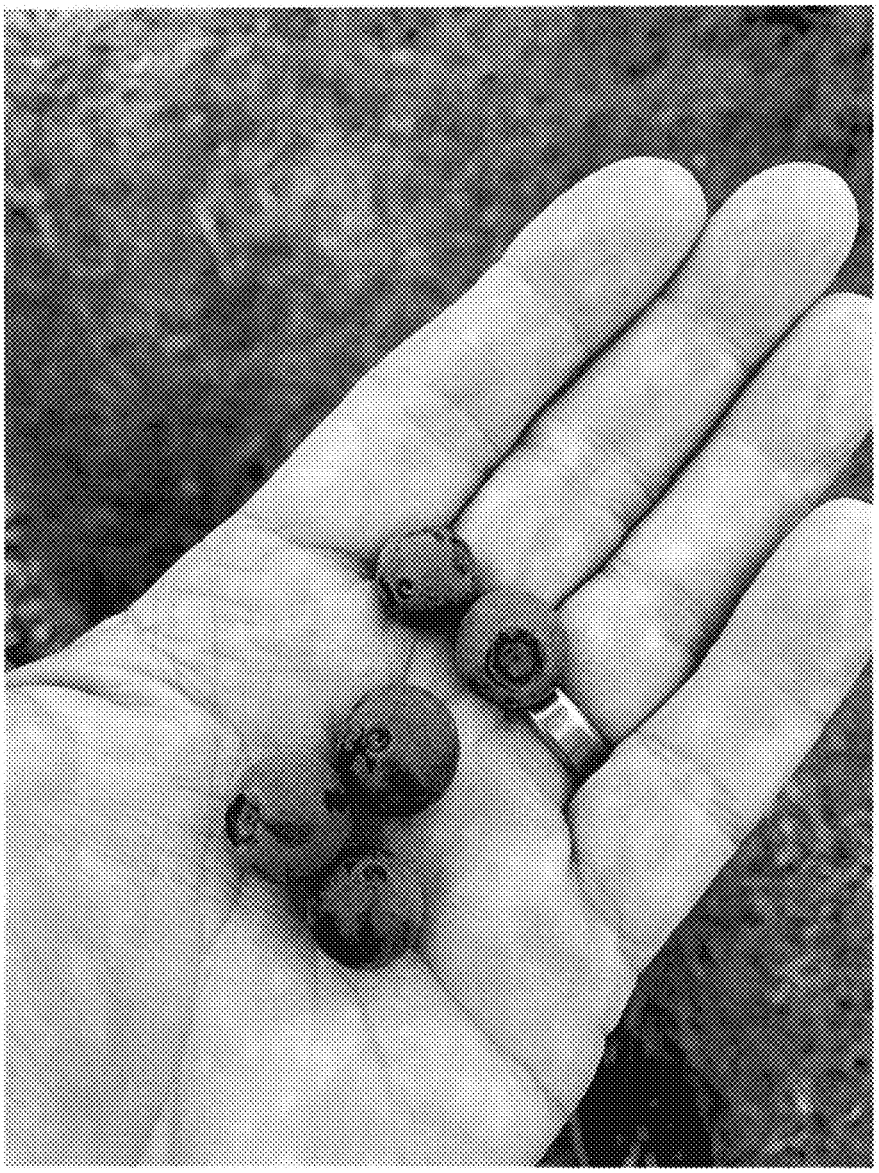

The photograph labeled FIG. 6 depicts a close-up view of ripe fruit of 'TH-1093' in a human hand, illustrating the relative size of the fruit taken in May 2021.

DETAILED BOTANICAL DESCRIPTION

The following traits have been consistently observed in the original plant of this new variety and in asexually propagated progeny grown in Alapaha and Griffin, Ga., and, to the best knowledge of the inventor, their combination forms the unique characteristics of the new variety *Vaccinium corymbosum* 'TH-1093'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-1093'. Where dimensions, sizes, colors, and other characteristics are given, it is to be understood that such characteristics are approximations and averages set forth as accurately as practicable. Data were collected between the years of 2013-2021 from horticulture farms and nurseries in Alapaha, Ga. from 3 to 6-year-old plants (planted in the field with supplemental irrigation). In this region, the long-term average annual low temperature ranges from about 54° F. to 58° F., and the average annual high temperature for the year ranges from about 78° F. to 82° F.

Botanical classification: *Vaccinium corymbosum* 'TH-1093'.

*Commercial classification*.—Fruit-bearing shrub.

*Parentage*.—Open-pollinated cross of 'MS-840' (non-patented breeding selection, female parent) and unknown male parent.

Growth and propagation:

*Propagation type*.—Vegetative by softwood cuttings.

*Growth rate*.—Plants are moderately vigorous, canopy tends to be more open, especially in younger plants.

*Root description*.—Fibrous.

Plant description:

*Growth habit*.—Plant is semi-spreading. Two to 4 main canes arising from narrow crown, and multiple branching of shoots from those canes about 10 to 15 cm above ground.

*Usage*.—Primarily for home garden usage.

*Productivity*.—High yielding. Yields of about 5 to 9 lbs per plant each year on plants 4 years old or older grown under well fertilized and irrigated field conditions. Frost protection may be useful to reach yield potential in some years.

*Size of plant*.—Plant is about 1.3 to 1.6 m tall by about 4 years. The plant crown, or base, is very narrow, typically about 10 to 15 cm in diameter. Upper portion of plant canopy reaches about 1.2 to 1.4 m in diameter by about 4 years.

*Cold hardiness*.—Similar to other early ripening southern highbush varieties such as 'Suziblue' (U.S. Plant Pat. No. 21,167) and 'Rebel' (U.S. Plant Pat. No. 18,138).

*Disease resistance*.—No notable disease resistance or susceptibility observed. Typical for early season southern highbush such as 'Suziblue' and 'Rebel'.

*Chilling requirement*.—Plants are medium chill, requiring about 350 to 450 hours, or more, of temperatures at or below 45° F. (7° C.) to induce normal leafing and flowering during the spring under conventional dormant production systems. The chill requirement is somewhat less than the female parent 'MS-840' (non-patented breeding selection; 450-550 hours of chilling required). The male parent is unknown.

*Leafing*.—Plants tend to break sufficient leaf buds simultaneously with, or shortly after, anthesis.

*Canes*.—Main cane base diameter about 15 to 25 mm, color most near Grey 201D; two year old cane diameter 10 to 15 mm, color transitioning from Yellow Green 145B to Greyed Orange 165A; current season wood diameter about 3 to 8 mm, color Yellow Green 145B.

*Fruiting wood*.—Moderate number of twigs (about 5 to 10 common) of about 10 to 15 cm in length, with internode lengths of about 15 to 25 mm common. Plants flower and fruit on one-year-old shoots.

Foliage:

*Leaf color healthy mature leaves*.—Top side of leaf color is Green N137C, under side of leaf color is Green 138B.

*Leaf arrangement*.—Alternate, simple.

*Leaf shape*.—Nearly elliptic.

*Leaf margins*.—Nearly entire.

*Leaf venation*.—Pinnate with slight netting.

*Leaf apices*.—Broadly acuminate.

*Leaf bases*.—Acute.

*Leaf dimensions*.—Length: about 45 to 65 mm; width: about 25 to 35 mm.

*Petioles*.—Small, about 2.5 to 3.0 mm long, about 1.5 to 2.0 mm wide; Color: Yellow Green 145C.

*Texture*.—Both upper and lower leaf surfaces, glaucous.

Flowers:

*Date of* 50% *anthesis*.—3-year average March 9 in southeast Georgia.

*Flower shape*.—Urceolate.

*Flower bud number*.—High, averaging about 4 to 6 buds per fruiting shoot.

*Flower bud anthocyanin coloration*.—Medium.

*Flowers per cluster*.—About 5 to 7 common.

*Flower fragrance*.—None detected.

*Corolla color*.—White NN 155C when fully opened; hints of White N155D can be observed just before fully opened.

*Corolla length*.—About 8.0 to 9.0 mm.

*Corolla width*.—About 5.0 to 6.0 mm.

*Corolla aperture width*.—About 2.5 to 4.0 mm.

*Flower peduncle*.—Length about 4.0 to 7.0 mm; Color: Green 138D to Yellow Green 145D.

*Flower pedicel*.—Length about 2.0 to 3.0 mm; Color: Green 138D.

*Calyx* (*with sepals*).—Diameter: about 6.0 to 7.0 mm; Color: sepals Green 138D; calyx center Green 138C.

*Stamen*.—Length: about 6.5 to 7.5 mm; number per flower: about 10; filament color: Green White 157C.

*Style*.—Length: about 7.5 to 8.5 mm; Color: Yellow Green 145C.

*Pistil*.—Length: about 9.0 to 10.5 mm; ovary color: Green 138C.

*Anther*.—Length: about 4.0 to 5.0 mm; number: 10; Color: Greyed Orange 165B to 165C.

*Pollen*.—Abundance: medium to high; Color: Yellow White 158B.

*Compatibility*.—The cultivar has a moderate degree of self-compatibility.

Fruit:

*Date of* 50% *maturity*.—3-year average around May 11 in southeast Georgia.

*Fruit development period*.—About 62 days in southeast Georgia.

*Berry color*.—With wax Violet Blue 98D; with wax removed Black 203C.

*Berry flesh color*.—White 155C.

*Berry surface wax abundance*.—High.

*Berry weight*.—$1^{st}$ harvest: about 1.8 to 2.2 g; $2^{nd}$ harvest: about 1.5 to 1.8 g.

*Berry size*.—Height from calyx to scar: about 14 to 16 mm; diameter: about 14 to 17 mm.

*Berry shape*.—Nearly spherical.

*Fruit stem scar*.—Small, dry, with little or no tearing upon harvest.

*Fruit calyx*.—Depth shallow, less than 1.0 mm, most often flat; width medium, about 5.0 to 7.0 mm; sepals often not present; turned mostly inwards and flat when present;, less than about 1.0 mm.

*Berry firmness*.—Very firm.

*Berry flavor and texture*.—Aromatic; sweet, mildly acid flavor; texture is semi-crisp, with a snap while eating.

*Storage quality*.—Very good.

*Suitability for mechanical harvesting*.—Not likely suitable.

*Uses*.—Primarily to be used in home garden market.

Seed:

*Seed abundance in fruit*.—Low, typically with about 5 or less fully developed seeds per berry.

*Seed color*.—Greyed Orange 166B to 166C.

*Seed dry weight*.—About 48.6 mg per 100 seed.

*Seed size*.—About 1.0 to 1.5 mm long.

It is claimed:

1. A new and distinct cultivar of the *Vaccinium* plant named 'TH-1093' as illustrated and described herein.

* * * * *